United States Patent
Thirumalai Rajan et al.

(10) Patent No.: US 10,144,710 B2
(45) Date of Patent: Dec. 4, 2018

(54) PROCESS FOR THE PREPARATION OF 4-[-({[4-CHOLORO-3(TRIFLUOROMETHYL) PHENYL]CARBAMOYL}AMINO)-3-FLUOROPHENOXY]-N-METHYLPYRIDINE-2-CARBOXAMIDE AND ITS POLYMORPHS THEREOF

(71) Applicants: MSN LABORATORIES PRIVATE LIMITED, Hyderabad, Telangana (IN); Srinivasan Thirumalai Rajan, Hyderabad, Telangana (IN); Sajja Eswaraiah, Hyderabad, Telangana (IN); Gutta Madhusudhan, Hyderabad, Telangana (IN)

(72) Inventors: Srinivasan Thirumalai Rajan, Telangana (IN); Sajja Eswaraiah, Telangana (IN); Gutta Madhusudhan, Telangana (IN)

(73) Assignee: MSN LABORATORIES PRIVATE LIMITED, Hyderabad, Telangana (IN)

(*) Notice: Subject to any disclaimer, the term of this patent is extended or adjusted under 35 U.S.C. 154(b) by 0 days.

(21) Appl. No.: 15/515,109

(22) PCT Filed: Sep. 29, 2015

(86) PCT No.: PCT/IN2015/000373
§ 371 (c)(1),
(2) Date: Mar. 28, 2017

(87) PCT Pub. No.: WO2016/051422
PCT Pub. Date: Apr. 7, 2016

(65) Prior Publication Data
US 2017/0247331 A1 Aug. 31, 2017

(30) Foreign Application Priority Data
Sep. 29, 2014 (IN) .......................... 4841/CHE/2014

(51) Int. Cl.
*C07D 213/81* (2006.01)

(52) U.S. Cl.
CPC .................. *C07D 213/81* (2013.01)

(58) Field of Classification Search
None
See application file for complete search history.

(56) References Cited

FOREIGN PATENT DOCUMENTS

WO WO-2005009961 A2 * 2/2005 ........... C07D 213/81

OTHER PUBLICATIONS

Liu et al, Fine Chemical Intermediates, vol. 42, No. 6, pp. 31-34, Dec. 2012.*
Written Opinion for PCT/IN2015/ 00373, dated Mar. 7, 2016.*

* cited by examiner

*Primary Examiner* — Zinna Northington Davis
(74) *Attorney, Agent, or Firm* — Seyfarth Shaw LLP

(57) ABSTRACT

The present invention relates to a process for the preparation of 4-[4-({[4-chloro-3-(trifluoromethyl)phenyl]carbamoyl}amino)-3-fluophenoxy]-N-methylpyridine-2-caroxamide compound of formula-I, its amorphous form and its crystalline polymorph-I which is represented by the following structural formula: (I)

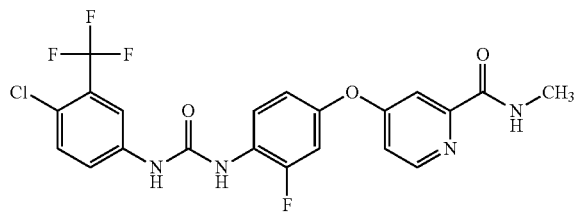

11 Claims, 2 Drawing Sheets

PROCESS FOR THE PREPARATION OF 4-[-({[4-CHOLORO-3(TRIFLUOROMETHYL) PHENYL]CARBAMOYL}AMINO)-3-FLUOROPHENOXY]-N-METHYLPYRIDINE-2-CARBOXAMIDE AND ITS POLYMORPHS THEREOF

RELATED APPLICATIONS

This application is a national phase application under 35 U.S.C. § 371 of International Application Number PCT/IN2015/000373, filed on Sep. 29, 2015, which claims priority to Indian Patent Application Numbers 4841/CHE/2014 filed on Sep. 29, 2014 and 4967/CHE/2015 filed on Sep. 18, 2015; the disclosures of all of which are hereby incorporated by reference in their entirety.

FIELD OF THE INVENTION

The present invention relates to a process for the preparation of 4-[4-({[4-chloro-3-(trifluoromethyl)phenyl]carbamoyl}amino)-3-fluorophenoxy]-N-methylpyridine-2-carboxamide compound of formula-1, its amorphous form and its crystalline polymorph-I which is represented by the following structural formula:

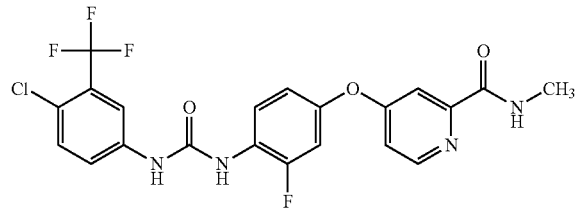

Formula-1

Further, the present invention provides a novel DMSO solvate of 4-[4-({[4-chloro-3-(trifluoromethyl)phenyl]carbamoyl}amino)-3-fluorophenoxy]-N-methylpyridine-2-carboxamide compound of formula-1 and its process for the preparation.

BACKGROUND OF THE INVENTION

4-[4-({[4-chloro-3-(trifluoromethyl)phenyl]carbamoyl}amino)-3-fluorophenoxy]-N-methylpyridine-2-carboxamide commonly known as Regorafenib. Regorafenib is marketed under the brand name Stivarga by Bayer Healthcare. It is approved in United States as Regorafenib monohydrate on 27 Sep. 2012. Regorafenib is indicated for the treatment of patients with metastatic colorectal cancer (CRC).

U.S. Pat. No. 7,351,834 B1 generically discloses Regorafenib, a pharmaceutically acceptable salt thereof, but there is no specific disclosure of Regorafenib in said patent or its equivalents. The patent discloses a process for the preparation of desfluoro analog of Regorafenib i.e. Sorafenib, involving the reaction of 4-chloro-3-(trifluoromethyl)phenyl isocyanate with 4-(2-(N-methylcarbamoyl)-4-pyridyloxy) aniline in dichloromethane.

U.S. Pat. No. 8,637,553 B2 A1 specifically discloses Regorafenib, pharmaceutically acceptable salts thereof and its composition thereof. Also discloses the process for the preparation of Regorafenib by reacting 4-(4-amino-3-fluorophenoxy) pyridine-2-carboxylic acid methylamide in toluene with 4-chloro-3-(trifluoromethyl) phenyl isocyanate. The reaction mass was concentrated under reduced pressure and the residue was triturated with diethyl ether. The resulting solid was collected by filtration and dried to afford Regorafenib.

WO 2005/009961 disclosed Regorafenib and its process for the preparation. The monohydrate of said compound is disclosed in WO 08/043446.

WO 2005/009961 is also disclosed polymorph-I of Regorafenib, US2010/0113533A1 disclosed the polymorph-II of Regorafenib and US2010/0063112A1 disclosed polymorph-III of Regorafenib and process for the preparation thereof.

Polymorphism is the occurrence of different solid state forms of a single compound and it is a property of some compounds and complexes. Thus, polymorphs are distinct solids having the same molecular formula and different physical properties such as different solubility profiles, different melting point temperatures and/or different x-ray diffraction peaks. Since the solubility of each polymorph may vary, identifying the existence of pharmaceutical polymorphs is essential for providing pharmaceuticals with desired solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction and by other methods such as, infrared spectrometry and differential scanning calorimetry. Solvent medium and mode of crystallization play very important role in obtaining a polymorphic form over the other.

Most of the prior reported processes for the preparation of Regorafenib compound of formula-1 provide Regorafenib with higher level of impurities which are toxic in nature. Especially, 4-(4-amino-3-fluorophenoxy)-N-methylpicolinamide compound of formula-4 remains as impurity in, the final API. Further it requires number of purifications to reduce or remove the said impurity.

In view of the above, there is a need in the art to develop a process for the preparation of Regorafenib compound of formula-1 which controls the level of above said genotoxic impurities and enhances the purity of the desired compound thereby useful for the pharmaceutical composition.

The present inventors have developed a process for the preparation of Regorafenib and surprisingly got Regorafenib with desired purity by simple modifications.

The present invention relates to a process for the preparation of crystalline polymorph-I of 4-[4-({[4-chloro-3-(trifluoromethyl)phenyl]carbamoyl]amino)-3-fluorophenoxy]-N-methylpyridine-2-carboxamide compound of formula-1 through its DMSO solvate of compound of formula-1 which controls the level of genotoxic impurities thereby meets the desired ICH quality.

The present invention also relates to an amorphous form of 4-[4-({[4-chloro-3-(trifluoromethyl)phenyl]carbamoyl]amino)-3-fluorophenoxy]-N-methylpyridine-2-carboxamide and its process.

BRIEF DESCRIPTION OF THE INVENTION

The first aspect of the present invention is to provide a process for the preparation of 4-[4-({[4-chloro-3-(trifluoromethyl)phenyl]carbamoyl}amino)-3-fluorophenoxy]-N-methyl pyridine-2-carboxamide compound of formula-1 substantially free of genotoxic impurity such as 4-(4-amino-3-fluorophenoxy)-N-methylpicolinamide compound of formula-4.

The second aspect of the present invention relates to DMSO solvate of 4-[4-({[4-chloro-3-(trifluoromethyl)phenyl]carbamoyl}amino)-3-fluorophenoxy]-N-methylpyridine-2-carboxamide compound of formula-1, hereinafter designated as crystalline Form-M.

The third aspect of the present invention is to provide a process for the preparation of DMSO solvate of 4-[4-({[4-chloro-3-(trifluoromethyl)phenyl]carbamoyl}amino)-3-fluorophenoxy]-N-methyl pyridine-2-carboxamide compound of formula-1.

The fourth aspect of the present invention is to provide a process for the preparation of crystalline polymorph-I of 4-[4-({4-chloro-3-(trifluoromethyl)phenyl] carbamoyl}amino)-3-fluorophenoxy]-N-methyl pyridine-2-carboxamide compound of formula-1.

The fifth aspect of the present invention relates to an improved process for the preparation of 4-(4-amino-3-fluorophenoxy)-N-methylpicolinamide compound of formula-4.

The sixth aspect of the present invention relates to an amorphous 4-[4-({4-chloro-3-(trifluoromethyl)phenyl] carbamoyl}amino)-3-fluorophenoxy]-N-methylpyridine-2-carboxamide compound of formula-1.

The seventh aspect of the present invention is to provide a process for the preparation of an amorphous 4-[4-({4-chloro-3-(trifluoromethyl)phenyl]carbamoyl}amino)-3-fluorophenoxy]-N-methylpyridine-2-carboxamide compound of formula-1.

The eighth aspect of the present invention is to provide a process for the preparation of 4-[4-({4-chloro-3-(trifluoromethyl)phenyl]carbamoyl}amino)-3-fluorophenoxy]-N-methylpyridine-2-carboxamide premix.

DETAILED DESCRIPTION OF THE INVENTION

Figure 1:
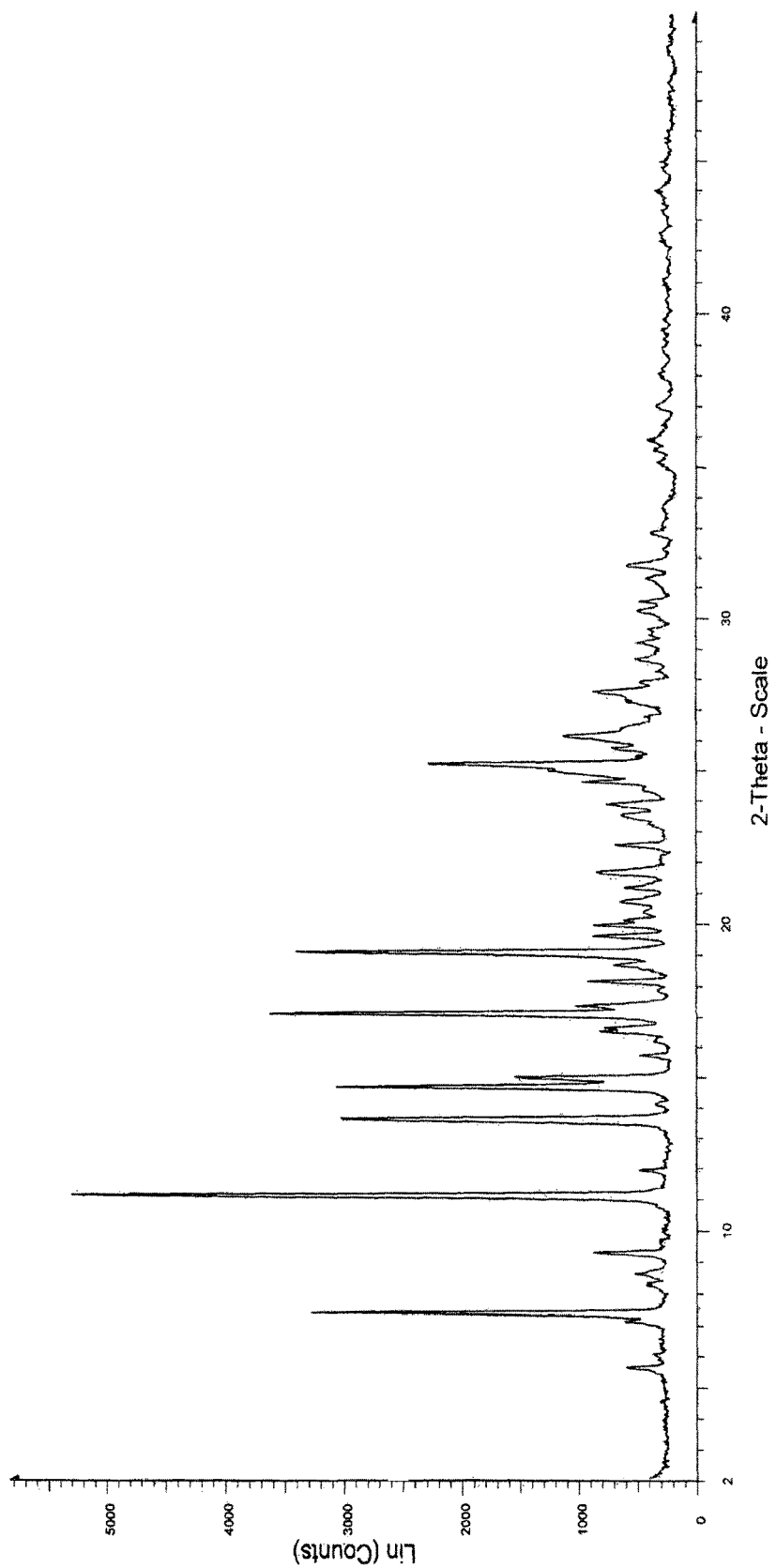
FIG. 1: Illustrates the powder X-ray diffractogram of DMSO solvate (crystalline form-M) of 4-[4-({4-chloro-3-(trifluoromethyl)phenyl]carbamoyl}amino)-3-fluorophenoxy]-N-methylpyridine-2-carboxamide compound of formula-1.

The term "suitable solvent" used in the present invention refers to "hydrocarbon solvents" such as n-pentane, n-hexane, n-heptane, cyclohexane, pet ether, benzene, toluene, xylene and the like; "ether solvents" such as dimethyl ether, diethyl ether, diisopropyl ether, methyl tert-butyl ether, 1,2-dimethoxyethane, tetrahydrofuran, 1,4-dioxane and the like; "ester solvents" such as methyl acetate, ethyl acetate, n-propyl acetate, isopropyl acetate, n-butyl acetate, isobutyl acetate, tert-butyl acetate and the like; "polar-aprotic solvents" such as dimethylacetamide, dimethylformamide, dimethylsulfoxide, N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcohol solvents" such as methanol, ethanol, n-propanol, iso-propanol, n-butanol, iso-butanol, t-butanol, ethane-1,2-diol, propane-1,2-diol and the like; "polar solvents" such as water; formic acid, acetic acid or mixture of any of the aforementioned solvents.

The term "suitable base" used in the present invention refers to "inorganic bases" selected from "alkali metal carbonates" such as sodium carbonate, potassium carbonate, lithium carbonate, cesium carbonate and the like; "alkali metal bicarbonates" such as sodium bicarbonate, potassium bicarbonate, lithium bicarbonate, cesium bicarbonate and the like; "alkali metal hydroxides" such as sodium hydroxide, potassium hydroxide, lithium hydroxide and the like; "alkali metal alkoxides" such as sodium methoxide, sodium ethoxide, potassium methoxide, potassium ethoxide, lithium methoxide, lithium ethoxide, sodium tert.butoxide, potassium tert.butoxide, lithium tert.butoxide and the like; "alkali metal hydrides" such as sodium hydride, potassium hydride, lithium hydride and the like; "alkali metal amides" such as sodium amide, potassium amide, lithium amide and the like; alkali metal and alkali earth metal salts of acetic acid such as sodium acetate, potassium acetate, magnesium acetate, calcium acetate and the like; ammonia; "organic bases" like dimethylamine, diethylamine, diisopropyl mine, diisopropylethylamine, diisobutylamine, triethylamine, tri isopropyl amine, tributylamine, tert.butyl amine, pyridine, 4-dimethylaminopyridine (DMAP), imidazole, N-methylimidazole, 1,8-diazabicyclo [5.4.0] undec-7-ene (DBU), 1,5-diazabicyclo [4.3.0]non-5-ene (DBN), N-methylmorpholine (NMM), 1,4-diazabicyclo[2.2.2]octane (DABCO), 2,6-lutidine and the like; "organolithium bases" such as methyl lithium, n-butyl lithium, lithium diisopropylamide (LDA) and the like; "organosilicon bases" such as lithium hexamethyldisilazide (LiHMDS), sodium hexamethyldisilazide (NaHMDS), potassium hexamethyldisilazide (KHMDS) and the like or their mixtures.

As used herein "substantially free of genotoxic impurities" refers to compound of formula-1 containing genotoxic impurity i.e., compound of formula-4, in an amount of less than about 0.005 area %, preferably in an amount less than 0.001 area % by HPLC.

The first aspect of the present invention is to provide a process for the preparation of 4-[4-({[4-chloro-3-(trifluoromethyl)phenyl]carbamoyl}amino)-3-fluorophenoxy]-N-methyl pyridine-2-carboxamide compound of formula-1 substantially free of genotoxic impurity such as 4-(4-amino-3-fluorophenoxy)-N-methylpicolinamide compound of formula-4, comprising of:
a) Reacting 4-chloro-N-methylpicolinamide compound of formula-2 with 4-amino-3-fluorophenol compound of formula-3 in presence of a suitable base in a suitable solvent in presence or absence of a suitable catalyst provides 4-(4-amino-3-fluorophenoxy)-N-methylpicolinamide compound of formula-4,
b) adding first lot of compound of formula-4 to the first lot of 4-chloro-3-(trifloromethyl)phenyl isocyanate compound of formula-5 in dichloromethane,
c) stirring the reaction mixture at a suitable temperature,
d) adding second lot of 4-(4-amino-3-fluorophenoxy)-N-methylpicolinamide compound of formula-4 to the reaction mixture,
e) stirring the reaction mixture at a suitable temperature and filtering the precipitated solid, f) dissolving the compound obtained in step-(e) in dimethylsulfoxide,
g) adding second lot of 4-chloro-3-(trifloromethyl)phenyl isocyanate compound of formula-5 to the reaction mixture and stirring the reaction mixture at a suitable temperature,
h) adding methanol to the reaction mixture,
i) cooling and stirring the reaction mixture,
j) filtering the precipitated solid and drying to get DMSO solvate of 4-(4-amino-3-fluorophenoxy)-N-methylpicolinamide compound of formula-1, k) dissolving DMSO solvate obtained in step-(j) in dimethylsulfoxide,
l) adding methanol to the reaction mixture and filtering the reaction mixture,
m) stirring the reaction mixture at −15 to −25° C.,
n) filtering the precipitated solid and drying the compound to get compound of formula-1,
o) optionally, slurrying the solid obtained in step-(n) in methanol to provide compound of formula-1 substantially free of genotoxic impurity such as 4-(4-amino-3-fluorophenoxy)-N-methylpicolinamide compound of formula-4.

Wherein, the suitable base used in step-(a) is selected from organic or inorganic base defined as above.

The suitable solvent used in step-(a) is selected from the list of solvents defined as above.

The suitable catalyst used in step-(a) is selected from tetraalkyl/aryl ammonium halides, tetraalkyl/aryl ammonium hydroxides and the like.

The preferred embodiment of the present invention provides a process for the preparation of 4-[4-({[4-chloro-3-(trifluoromethyl)phenyl]carbamoyl}amino)-3-fluoro phenoxy]-N-methyl pyridine-2-carboxamide compound of formula-1 substantially free of genotoxic impurity such as 4-(4-amino-3-fluorophenoxy)-N-methylpicolinamide compound of formula-4, comprising of:
  a) Reacting 4-chloro-N-methylpicolinamide compound of formula-2 with 4-amino-3-fluorophenol compound of formula-3 in presence of a suitable base in a suitable solvent in presence or absence of a suitable catalyst provides 4-(4-amino-3-fluorophenoxy)-N-methylpicolinamide compound of formula-4,
  b) adding first lot of 4-(4-amino-3-fluorophenoxy)-N-methylpicolinamide compound of formula-4 to first lot of 4-chloro-3-(trifluoromethyl)phenyl isocyanate in dichloromethane,
  c) stirring the reaction mixture at 0-5° C.,
  d) adding second lot of 4-(4-amino-3-fluorophenoxy)-N-methylpicolinamide compound of formula-4 to the reaction mixture,
  e) stirring the reaction mixture at 0-5° C. and filtering the precipitated solid,
  f) dissolving the compound obtained in step-(e) in dimethylsulfoxide,
  g) adding second lot of 4-chloro-3-(trifloromethyl)phenyl isocyanate compound of formula-5 to the reaction mixture and stirring the reaction mixture at 19° C.-23° C.,
  h) adding methanol to the reaction mixture,
  i) cooling and stirring the reaction mixture,
  j) filtering the precipitated solid and drying to get DMSO solvate of 4-(4-amino-3-fluorophenoxy)-N-methylpicolinamide compound of formula-1,
  k) dissolving DMSO solvate obtained in step-(j) in dimethylsulfoxide,
  l) adding methanol to the reaction mixture and filtering the reaction mixture,
  m) stirring the reaction mixture at −15 to −25° C.,
  n) filtering the solid and drying the compound to get compound of formula-1,
  o) slurrying the solid obtained in step-(n) in methanol provides compound of formula-1 substantially free of genotoxic impurity such as 4-(4-amino-3-fluorophenoxy)-N-methylpicolinamide compound of formula-4.

The second aspect of the present invention provides DMSO solvate of 4-[4-({[4-chloro-3-(trifluoromethyl)phenyl]carbamoyl}amino)-3-fluorophenoxy]-N-methyl pyridine-2-carboxamide compound of formula-1, hereinafter designated as crystalline Form-M. Further, the crystalline form-M is characterized by:
  a) its powder X-ray diffraction pattern having peaks at 7.3, 9.2, 11.0, 13.5, 14.6, 14.9, 16.5, 17.0, 17.3, 18.1, 19.0, 19.5, 19.9, 21.6, 23.8, 24.6, 24.9, 25.1, 26.1 and 27.5±0.2 degrees of 2-theta; and
  b) its powder X-ray diffraction pattern as illustrated in FIG. 1.

The third aspect of the present invention is to provide a process for the preparation of DMSO solvate of 4-[4-({[4-chloro-3-(trifluoromethyl)phenyl]carbamoyl}amino)-3-fluorophenoxy]-N-methyl pyridine-2-carboxamide compound of formula-1, comprising of:
  a) Adding first lot of 4-(4-amino-3-fluorophenoxy)-N-methylpicolinamide compound of formula-4 with 4-chloro-3-(trifloromethyl)phenyl isocyanate compound of formula-5 in a suitable solvent,
  b) stirring the reaction mixture at a suitable temperature,
  c) adding another lot of 4-(4-amino-3-fluorophenoxy)-N-methylpicolinamide compound of formula-4 to the reaction mixture,
  d) stirring the reaction mixture at a suitable temperature,
  e) filtering the solid obtained in step-(d),
  f) dissolving the compound obtained in step-(e) in dimethylsulfoxide,
  g) adding a suitable solvent to the reaction mixture,
  h) cooling and stirring the reaction mixture,
  i) filtering the solid and drying to get DMSO solvate of compound of formula-1

Wherein, the suitable solvent is selected from chloro solvents, polar-aprotic solvents and alcohol solvents defined as above.

The preferred embodiment of the present invention provides a process for the preparation of DMSO solvate of 4-[4-({[4-chloro-3-(trifluoromethyl)phenyl]carbamoyl}amino)-3-fluorophenoxy]-N-methyl pyridine-2-carboxamide compound of formula-1, comprising of:
  a) Adding first lot of 4-(4-amino-3-fluorophenoxy)-N-methylpicolinamide compound of formula-4 with 4-chloro-3-(trifloromethyl)phenyl isocyanate compound of formula-5 in dichloromethane,
  b) stirring the reaction mixture at 0-5° C.,
  c) adding another lot of 4-(4-amino-3-fluorophenoxy)-N-methylpicolinamide compound of formula-4 to the reaction mixture,
  d) stirring the reaction mixture at 0-5° C.,
  e) filtering the solid obtained in step-(d),
  f) dissolving the compound obtained in step-(e) in dimethylsulfoxide,
  g) adding methanol to the reaction mixture,
  h) cooling and stirring the reaction mixture,
  i) filtering the solid and drying to get DMSO solvate of compound of formula-1.

The fourth aspect of the present invention is to provide a process for the preparation of crystalline polymorph-I of 4-[4-({[4-chloro-3-(trifluoromethyl)phenyl]carbamoyl}amino)-3-fluorophenoxy]-N-methyl pyridine-2-carboxamide compound of formula-1, comprising of:
  a) Dissolving DMSO solvate of compound of formula-1 in dimethylsulfoxide,
  b) adding anti-solvent to the reaction mixture,
  c) cooling and stirring the reaction mixture at a suitable temperature,
  d) filtering the solid and drying the compound to get crystalline polymorph-I of compound of formula-1, e) optionally, slurrying the solid obtained in step-(d) in a suitable solvent to provide crystalline polymorph-I of compound of formula-1.

Wherein, the suitable anti-solvent is a solvent selected from polar-aprotic solvents and alcohol solvents defined as above.

The preferred embodiment of the present invention provides a process for the preparation of crystalline polymorph-I of 4-[4-({[4-chloro-3-(trifluoromethyl)phenyl]carbamoyl}amino)-3-fluorophenoxy]-N-methylpyridine-2-carboxamide compound of formula-1, comprising of:
 a) Dissolving DMSO solvate of compound of formula-1 in dimethylsulfoxide,
 b) adding methanol to the reaction mixture,
 c) cooling and stirring the reaction mixture at −15 to −25° C.,
 d) filtering the solid and drying the compound to get crystalline polymorph-I of compound of formula-1,
 e) slurrying the solid obtained in step-(d) in methanol to provide crystalline polymorph-I of compound of formula-1.

Most of the prior reported process for the preparation of Regorafenib compound of formula-1 provides Regorafenib with higher level of impurities which are toxic in nature and requires number of purifications to control the said impurities. Even though, some of the impurities are not reduced/controlled by the known purification techniques. Hence, these prior reported processes are not suitable for use in the pharmaceutical composition. In view of this, the present inventors have developed an improved process i.e., re-reaction technique for the preparation of Regorafenib compound of formula-1 which controls the level of genotoxic impurities thereby meets the desired ICH quality. Hence, it can be known that, the process of the present invention is more advantageous than the prior art processes.

The fifth aspect of the present invention is to provide an improved process for the preparation of 4-(4-amino-3-fluorophenoxy)-N-methylpicolinamide compound of formula-4 comprising of reacting 4-chloro-N-methylpicolinamide compound of formula-2 with 4-amino-3-fluorophenol compound of formula-3 in presence of a suitable base in a suitable solvent in presence or absence of a suitable phase transfer catalyst provides 4-(4-amino-3-fluorophenoxy)-N-methylpicolinamide compound of formula-4.

Wherein, the suitable base is selected from organic or inorganic base defined as above; the suitable solvent is selected from the list of solvents defined as above.

The suitable phase transfer catalyst is selected from tetraalkyl/aryl ammonium halides, tetraalkyl/aryl ammonium hydroxides and the like;

The preferred embodiment of the present invention provides an improved process for the preparation of 4-(4-amino-3-fluorophenoxy)-N-methylpicolinamide compound of formula-4, comprising of reacting 4-chloro-N-methylpicolinamide compound of formula-2 with 4-amino-3-fluorophenol compound of formula-3 in presence of potassium.tert.butoxide, potassium carbonate and tetrabutylammoniumbromide in acetonitrile provides 4-(4-amino-3-fluorophenoxy)-N-methylpicolinamide compound of formula-4.

Figure 2:
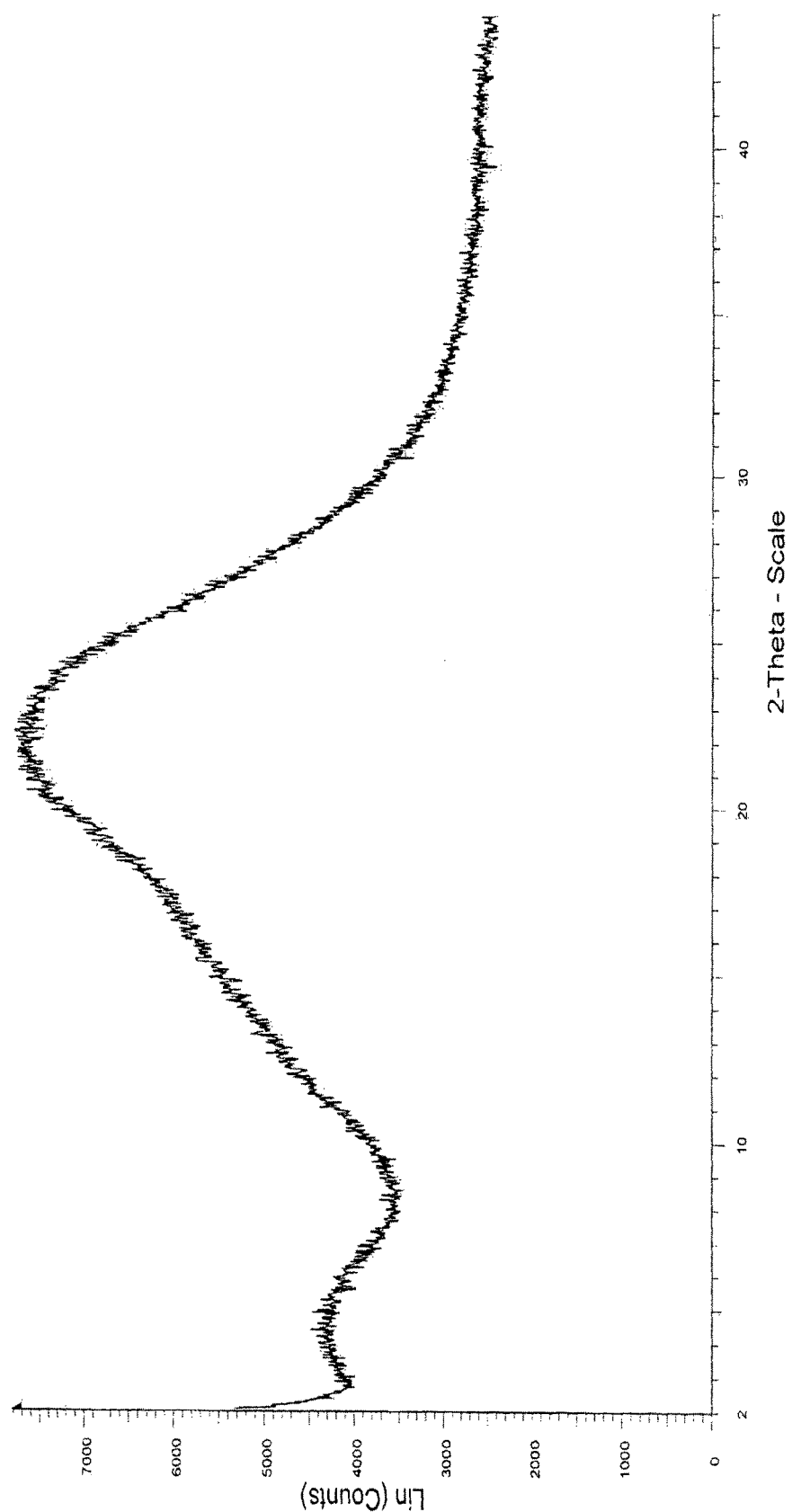
FIG. 2: Illustrates the powder X-ray diffractogram of amorphous 4-[4-({4-chloro-3-(trifluoromethyl)phenyl] carbamoyl}amino)-3-fluorophenoxy]-N-methylpyridine-2-carboxamide compound of formula-1.

The sixth aspect of the present invention relates to an amorphous 4[4-({[4-chloro-3-(trifluoromethyl)phenyl]carbamoyl}amino)-3-fluorophenoxy]-N-methylpyridine-2-carboxamide, characterized by powder X-ray diffraction pattern as illustrated in Figure-2.

The seventh aspect of the present invention provides a process for the preparation of amorphous 4-[4-({[4-chloro-3-(trifluoromethyl)phenyl]carbamoyl}amino)-3-fluorophenoxy]-N-methylpyridine-2-carboxamide, comprising the following steps of:
 a) Dissolving 4-[4-({[4-chloro-3-(trifluoromethyl)phenyl]carbamoyl}amino)-3-fluoro phenoxy]-N-methylpyridine-2-carboxamide in a suitable solvent,
 b) stirring the reaction mixture,
 c) filtering the reaction mixture,
 d) distilling off the solvent from the filtrate obtained in step-(c) to get amorphous 4-[4-({[4-chloro-3-(trifluoromethyl)phenyl]carbamoyl}amino)-3-fluorophenoxy]-N-methylpyridine-2-carboxamide.

Wherein, the suitable solvent used in step-a) is selected from ether solvents, ester, solvents, chloro solvents, hydrocarbon solvents, ketone solvents, polar aprotic solvents, nitrile solvents, alcohol solvents and polar solvents such as water and also mixtures thereof.

The preferred embodiment of the present invention provides a process for the preparation of amorphous 4-[4-({[4-chloro-3-(trifluoromethyl)phenyl]carbamoyl}amino)-3-fluorophenoxy]-N-methylpyridine-2-carboxamide, comprising the following steps of:
 a) Dissolving 4-[4-({[4-chloro-3-(trifluoromethyl)phenyl]carbamoyl}amino)-3-fluorophenoxy]-N-methylpyridine-2-carboxamide in tetrahydrofuran,
 b) stirring the reaction mixture,
 c) filtering the reaction mixture and washing with tetrahydrofuran,
 d) distilling off the solvent from the filtrate obtained in step-(c) to get amorphous 4-[4-({[4-chloro-3-(trifluoromethyl)phenyl]carbamoyl}amino)-3-fluorophenoxy]-N-methylpyridine-2-carboxamide.

Another preferred embodiment of the present invention provides a process for the preparation of amorphous 4-[4-({[4-chloro-3-(trifluoromethyl)phenyl]carbamoyl}amino)-3-fluorophenoxy]-N-methylpyridine-2-carboxamide, comprising the following steps of:
 a) Dissolving 4-[4-({[4-chloro-3-(trifluoromethyl)phenyl]carbamoyl}amino)-3-fluorophenoxy]-N-methylpyridine-2-carboxamide in a mixture of tetrahydrofuran and methanol,
 b) stirring the reaction mixture,
 c) filtering the reaction mixture,
 d) distilling off the solvent from the filtrate obtained in step-(c) to get amorphous 4-[4-({[4-chloro-3-(trifluoromethyl)phenyl]carbamoyl}amino)-3-fluorophenoxy]-N-methylpyridine-2-carboxamide.

The eighth aspect of the present invention provides a process for the preparation of amorphous 4-[4-({[4-chloro-3-(trifluoromethyl)phenyl]carbamoyl}amino)-3-fluorophenoxy]-N-methylpyridine-2-carboxamide premix, comprising the following steps of:
 a) Dissolving 4-[4-({[4-chloro-3-(trifluoromethyl)phenyl]carbamoyl}amino)-3-fluoro phenoxy]-N-methylpyridine-2-carboxamide in a suitable solvent,
 b) stirring the reaction mixture,
 c) filtering the reaction mixture,
 d) adding a suitable premixing agent to the filtrate obtained in step-(c),
 e) distilling off the solvent from the filtrate obtained in step-(d) to get amorphous 4-(4-({[4-chloro-3-(trifluoromethyl)phenyl]carbamoyl)amino)-3-fluorophenoxy]-N-methylpyridine-2-carboxamide premix.

Wherein, the suitable solvent used in step-a) is selected from ether solvents, ester solvents, chloro solvents, hydrocarbon solvents, ketone solvents, polar aprotic solvents, nitrile solvents, alcohol solvents and polar solvents such as water and also mixtures thereof.

The suitable premixing agent used in step-(d) is micro crystalline cellulose (MCC).

A preferred embodiment of the present invention provides a process for the preparation of amorphous 4-4-({[4-chloro-3-(trifluoromethyl)phenyl]carbamoyl}amino)-3-fluorophenoxy]-N-methylpyridine-2-carboxamide premix, comprising the following steps of:

a) Dissolving 4-[4-({[4-chloro-3-(trifluoromethyl)phenyl]carbamoyl}amino)-3-fluoro phenoxy]-N-methylpyridine-2-carboxamide in methyl ethyl ketone,
b) stirring the reaction mixture,
c) filtering the reaction mixture,
d) adding micro crystalline cellulose (MCC) to the filtrate obtained in step-(c),
e) distilling off the solvent from the filtrate obtained in step-(d) to get amorphous 4-[4-({[4-chloro-3-(trifluoromethyl)phenyl]carbamoyl}amino)-3-fluorophenoxy]-N-methylpyridine-2-carboxamide premix.

The 4-[4-({[4-chloro-3-(trifluoromethyl)phenyl]carbamoyl}amino)-3-fluorophenoxy]-N-methylpyridine-2-carboxamide used in the present invention can be prepared from the process disclosed in WO 2005/009961 or any of the process known in the art.

The amorphous 4-[4-({[4-chloro-3-(trifluoromethyl)phenyl]carbamoyl}amino)-3-fluorophenoxy]-N-methylpyridine-2-carboxamide obtained from the present invention can be used in the pharmaceutical composition as a medicament.

HPLC Method of Analysis:

Amorphous 4-[4-({[4-chloro-3-(trifluoromethyl)phenyl]carbamoyl}amino)-3-fluoro phenoxy]-N-methylpyridine-2-carboxamide Apparatus: A liquid chromatographic system is to be equipped with variable wavelength UV-detector; Column: Kromacil 100C18, 125×4.0 mm, 5 mm (or) equivalent; Flow rate: 1.2 ml/min; Wavelength: 250 nm; Column Temperature: 25° C.; Injection volume: 10 ml; Run time: 17 mins; Diluent: Acetonitrile: Water (98:02) v/v; Needle wash: Acetonitrile: Water (90:10) v/v; Elution: Gradient; Mobile phase-A: Buffer: Methanol (95:05 v/v); Mobile phase-B: Acetonitrile: Water (90:10) v/v. Weigh accurately about 1.36 g of potassium dihydrogen orthophosphate in 1000 ml of Milli-Q-water and filtered this solution through 0.22 m Nylon membrane filter paper.

4-[4-({[4-chloro-3-(trifluoromethyl)phenyl]carbamoyl}amino)-3-fluorophenoxy]-N-methylpyridine-2-carboxamide Apparatus: A liquid chromatographic system is to be equipped with variable wavelength UV-detector; Column: Kromacil 100-C18, 250×4.6 mm, 5 mm (or) equivalent; Wavelength: 240 nm; Column Temperature: 30° C.; Injection volume: 10 mL; Run time: 52 mins; Diluent: Acetonitrile: Water (98:02) v/v; Needle wash: Acetonitrile: Water (90:10) v/v; Elution: Gradient; Mobile phase-A: Buffer: Methanol (95:05 v/v); Mobile phase-B: Acetonitrile: Water (90:10) v/v. Weigh accurately about 1.36 g of potassium dihydrogen orthophosphate in 1000 ml of Milli-Q-water and filtered this solution through 0.22 μm Nylon membrane filter paper.

Amine Impurity, Chloro Impurity, Methyl Ester Impurity and Trifluoro Impurity Content by HPLC:

Apparatus: A liquid chromatographic system is to be equipped with variable wavelength PDA-detector; Column: Hyperclone BDS C18, 250×4.6 mm, 5 mm (or) equivalent; Wavelength: 210 nm & 240 nm; Column Temperature: 25° C.; Injection volume: 15 μL; Diluent: Methanol: Tetrahydrofuran; Needle wash: Acetonitrile: Water (90:10) v/v; Elution: Gradient; Mobile phase-A: Buffer (100%); Mobile phase-B: Acetonitrile: Water (90:10) v/v. Transfer accurately 1.5 mL of Perchloric acid into a 1000 mL of Milli-Q water and filter this solution through 0.22 mm nylon membrane filter paper.

PXRD analysis of amorphous and DMSO solvate of the 4-4-({[4-chloro-3-(trifluoromethyl)phenyl]carbamoyl}amino)-3-fluorophenoxy]-N-methylpyridine-2-carboxamide of the present invention was carried out by using BRUKER/AXS X-Ray diffractometer using Cu Kα radiation of wavelength 1.5406 A° and at continuous scan speed of 0.03°/min.

Differential scanning calorimetric (DSC) analysis was performed with Q10 V9.6 Build 290 calorimeter. Samples of about 2 to 3 milligrams held in a closed pan were analyzed at a heating rate of 10° C. per minute.

Water content of the amorphous 4-[4-({[4-chloro-3-(trifluoromethyl)phenyl]carbamoyl}amino)-3-fluorophenoxy]-N-methylpyridine-2-carboxamide of the present invention was measured by using a karl fisher titrator.

The amorphous 4-[4-({[4-chloro-3-(trifluoromethyl)phenyl]carbamoyl}amino)-3-fluorophenoxy]-N-methylpyridine-2-carboxamide and its crystalline polymorph-I which is obtained by the present invention can be further micronized or milled to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

The (4-(3-fluoro-4-[(2-fluoro-4-{[2-(methylcarbamoyl)pyridin-4-yl]oxy}phenyl) carbamoyl]amino}phenoxy)-N-methylpyridine-2-carboxamide) is known as "Dimer impurity" having the following structure:

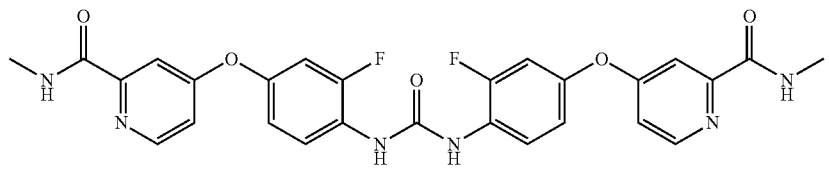

The 4-chloro-3-(trifluoromethyl)aniline is known as "Trifluoro impurity" having the following structure:

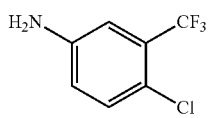

The methyl 4-chloropicolinate is known as "Methyl ester impurity" having the following structure:

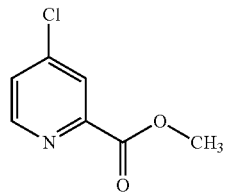

The process of the present invention controlled above said Dimer impurity, Trifluoro impurity & Methyl ester impurity to 0.01%, preferably to non-detectable level. The process of the present invention can be represented schematically as follows:

Scheme-I:

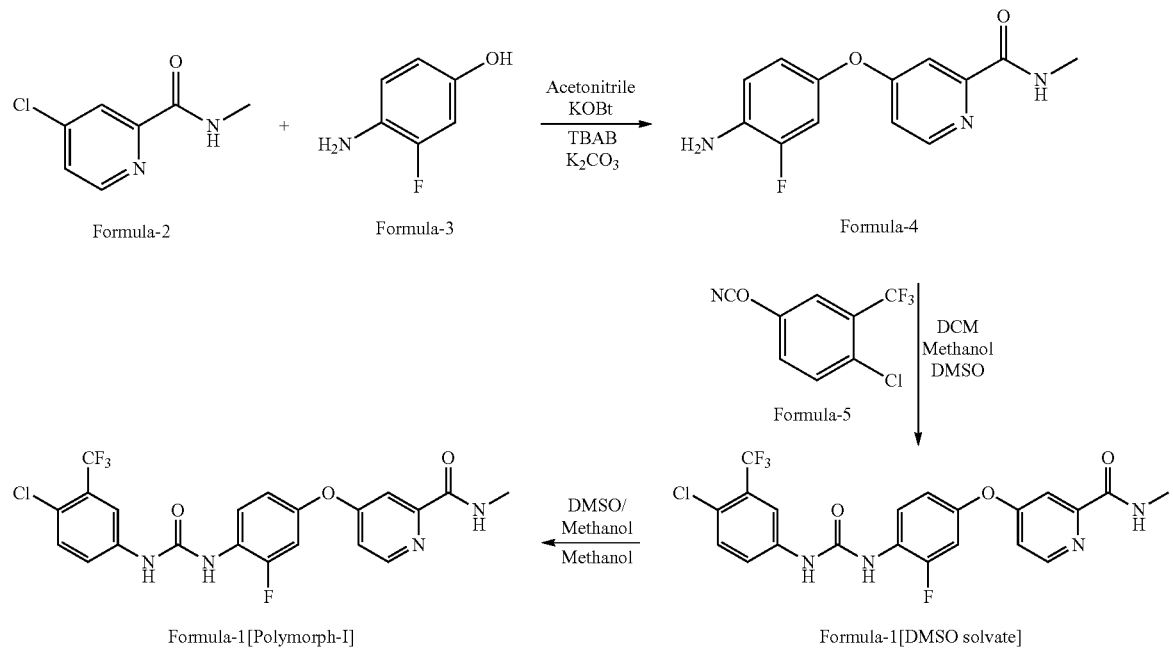

The process described in the present invention was demonstrated in examples illustrated below. These examples are provided as illustration only and therefore should not be construed as limitation of the scope of the invention.

EXAMPLES

Example-1: Preparation of 4-(4-amino-3-fluorophenoxy)-N-methylpicolinamide (Formula-4)

4-amino-3-fluorophenol (18.62 g), potassium tert.butoxide (20.6 g), potassium carbonate (10.2 g) & tetrabutylammonium bromide (9.5 g) were added to a pre-cooled acetonitrile (100 ml) at −10° C. to −15° C. under nitrogen atmosphere. Raised the temperature of the reaction mixture to 0° C. to 5° C. and stirred for 15 minutes. 4-chloro-N-methylpicolinamide (25 g) was added to the reaction mixture at the same temperature. Heated the reaction mixture to 80° C.–85° C. and stirred for 6 hours at the same temperature. Distilled off the 60% volume of the solvent under reduced pressure and cooled the reaction mixture to 25° C.–30° C. Pre-cooled water (150 ml) followed by dichloromethane (375 ml) were added to the reaction mixture and stirred for 15 minutes. Filtered the reaction mixture through hyflow bed and washed with dichloromethane. Separated both the aqueous and organic layers and extracted aqueous layer with dichloromethane. Combined the organic layers and washed with water. Distilled off the solvent completely and co-distilled the reaction mixture with acetonitrile. Added acetonitrile to the obtained compound at 25° C.–30° C. and cooled the reaction mixture to 0° C. to 5° C. and stirred for 60 minutes at the same temperature. Filtered the reaction mixture and washed the obtained compound with chilled acetonitrile. Water was added to the obtained compound and stirred the reaction mixture for 2 hours at 25° C.–30° C. Filtered the solid, washed with water and dried the compound to get the title compound. Yield: 25.25 g; M.R: 136-142° C.

Example-2: Preparation of DMSO Solvate of 4-[4-({[4-chloro-3-(trifluoromethyl)phenyl]carbamoyl}amino)-3-fluorophenoxy]-N-methylpyridine-2-carboxamide Compound of Formula-1

Step-a): Preparation of Compound of Formula-1
4-chloro-3-(trifloromethyl)phenyl isocyanate (318.0) and 4-(4-amino-3-fluorophenoxy)-N-methylpicolinamide (125 g) were added to a pre-cooled dichloromethane (2500 ml) at 0° C. to 5° C. under nitrogen atmosphere. Stirred the reaction mixture for 60 minutes at the same temperature. Another lot of 4-(4-amino-3-fluorophenoxy)-N-methyl picolinamide (125 g) was added to the reaction mixture at 0°

C. to 5° C. and stirred the reaction mixture for 3 hours. Filtered the solid and washed with dichloromethane and dried the compound at 35° C. to 40° C. for 4 hours to get the title compound. Yield: 350 g; Content of 4-(4-amino-3-fluorophenoxy)-N-methylpicolinamide: 704.13 ppm (0.070% by HPLC).

Step-b): Preparation of DMSO Solvate of Compound of Formula-1 (Re-Reaction)

The compound obtained in step-(a) was added to a pre-cooled dimethylsulfoxide (1400 ml) at 19° C. to 23° C. Second lot of 4-chloro-3-(trifloromethyl)phenyl isocyanate (29.67 g) was added to the reaction mixture at 19° C. to 23° C. and stirred for 1 hour. Raised the temperature of the reaction mixture to 25° C. to 30° C. and stirred the reaction mixture for 2 hours. Methanol (5600 ml) was slowly added to the reaction mixture at 25° C. to 30° C. Cooled the reaction mixture to −10° C. to −15° C. and stirred the reaction mixture for 2 hours at same temperature. Filtered the solid, washed with methanol and dried the compound to get Regorafenib [DMSO solvate]. Yield: 275 g; M.R: 196-202° C. DMSO content: 18%.

Content of 4-(4-amino-3-fluorophenoxy)-N-methylpicolinamide: 7.45 ppm (0.000745% by HPLC); Dimer impurity: 0.01%.

The PXRD of obtained compound is depicted in FIG. 1.

Example-3: Preparation of DMSO Solvate of 4-[4-({[4-chloro-3-(trifluoromethyl)phenyl]carbamoyl}amino)-3-fluorophenoxy]-N-methylpyridine-2-carboxamide Compound of Formula-1

4-chloro-3-(trifloromethyl)phenyl isocyanate (318.0 g) and first lot of 4-(4-amino-3-fluorophenoxy)-N-methylpicolinamide (125 g) were added to a pre-cooled dichloromethane (2500 ml) at 0° C. to 5° C. under nitrogen atmosphere. Stirred the reaction mixture for 60 minutes at the same temperature. Another lot of 4-(4-amino-3-fluorophenoxy)-N-methylpicolinamide (125 g) was added to the reaction mixture at 0° C. to 5° C. and stirred the reaction mixture for 3 hours. Filtered the solid and washed with dichloromethane and suck dry the compound. The obtained wet compound was added to a pre-cooled dimethylsulfoxide (1400 ml) at 19° C. to 23° C. Raised the temperature of the reaction mixture to 25° C. to 30° C. and stirred the reaction mixture for 2 hours. Methanol (5600 ml) was slowly added to the reaction mixture at 25° C. to 30° C. Cooled the reaction mixture to −10° C. to −15° C. and stirred the reaction mixture for 2 hours at same temperature. Filtered the solid, washed with methanol and dried the compound to get Regorafenib [DMSO solvate]. Yield: 275 g; M.R: 196-202° C. DMSO content: 18%.

Content of 4-(4-amino-3-fluorophenoxy)-N-methylpicolinamide: 7.45 ppm (0.000745% by HPLC); Dimer impurity: Not detected.

The PXRD of obtained compound is depicted in FIG. 1.

Example-4: Preparation of 4-[4-({[4-chloro-3-(trifluoromethyl)phenyl]carbamoyl}amino)-3-fluorophenoxy]-N-methylpyridine-2-carboxamide Compound of Formula-1

4-chloro-3-(trifloromethyl)phenyl isocyanate (60 g) and 4-(4-amino-3-fluorophenoxy)-N-methylpicolinamide (25 g) were added to a pre-cooled dichloromethane (500 ml) at 0° C. to 5° C. under nitrogen atmosphere. Stirred the reaction mixture for 60 minutes at the same temperature. Another lot of 4-(4-amino-3-fluorophenoxy)-N-methylpicolinamide (25 g) was added to the reaction mixture at 0° C. to 5° C. and stirred the reaction mixture for 3 hours. Filtered the solid and washed with dichloromethane and suck dry the compound. The obtained wet compound was added to a pre-cooled dimethylsulfoxide (300 ml) at 19° C. to 23° C. Raised the temperature of the reaction mixture to 25° C. to 30° C. and stirred the reaction mixture for 2 hours. Methanol (1000 ml) was slowly added to the reaction mixture at 25° C. to 30° C. Cooled the reaction mixture to 0° C. to 5° C. and stirred the reaction mixture for 2 hours at same temperature. Filtered the solid, washed with methanol and dried the compound to get Regorafenib. Yield: 75 g; M.R: 196-202° C.

Content of 4-(4-amino-3-fluorophenoxy)-N-methylpicolinamide: 7.45 ppm (0.000745% by HPLC); Dimer impurity: Not detected.

The PXRD of the obtained compound is matching with polymorph-I of Regorafenib disclosed in US201073953A1.

Example-5: Preparation of polymorph-I of 4-[4-({[4-chloro-3-(trifluoromethyl)phenyl]carbamoyl}amino)-3-fluorophenoxy]-N-methylpyridine-2-carboxamide Compound of Formula-1

125 g of Regorafenib in dimethylsulfoxide (500 ml) at 25° C. to 30° C. under nitrogen atmosphere. Methanol (1625 ml) was added to the reaction mixture at the same temperature. Filtered the reaction mixture through hyflow bed and washed with methanol. Cooled the reaction mixture to −15° C. to −20° C. and stirred the reaction mixture for 3 hours at the same temperature. Filtered the solid, washed with methanol.

Methanol (234.4 ml) was added the above wet compound at 25° C. to 30° C. and stirred the reaction mixture for 2 hours. Cooled the reaction mixture to 0° C. to 5° C. and stirred for 2 hours. Filtered the solid, washed with methanol and dried the compound to get Regorafenib. Yield: 106.25 g; M.R: 199-206° C. Purity: 99.98% by HPLC; Particle size distribution D90:46.6 pm. D[4.3]: 23.8 pm.

Content of 4-(4-amino-3-fluorophenoxy)-N-methylpicolinamide (Amine impurity): 2.0 ppm (0.0002% by HPLC); Chloro impurity compound of formula-2: 1.4 ppm (0.00014% by HPLC); 4-amino-3-fluorophenol impurity compound of formula-3: Not detected; Trifluoro impurity: Not detected; Methylester impurity: Not detected; Dimer impurity: Not detected.

The PXRD of the obtained compound is matching with polymorph-I of Regorafenib disclosed in US201073953A1.

Example-6: Preparation of polymorph-I of 4-[4-({[4-chloro-3-(trifluoromethyl)phenyl]carbamoyl}amino)-3-fluorophenoxy]-N-methylpyridine-2-carboxamide Compound of Formula-1

Dissolved Regorafenib (20 g) in methylethyl ketone (240 ml) at 25° C. to 30° C. Heated the reaction mixture to 70° C. to 75° C. and stirred for 30 minutes at the same temperature. Filtered the reaction mixture and washed with methylethyl ketone. Cooled the filtrate to 0° C. to 5° C. and stirred for 3 hours at the same temperature. Filtered the solid, washed with methylethyl ketone and dried to get the title compound. Yield: 15.2 g; M.R: 198-206° C.

The PXRD of the obtained compound is matching with polymorph-I of Regorafenib disclosed in US201073953A1.

Example-7: Preparation of amorphous 4-[4-({[4-chloro-3-(trifluoromethyl)phenyl]carbamoyl)amino)-3-fluorophenoxy]-N-methylpyridine-2-carboxamide Dissolved 4-[4-({[4-chloro-3-(trifluoromethyl)phenyl]carbamoyl}amino)-3-fluorophenoxy]-N-methylpyridine-2- carboxamide (1 g) in tetrahydrofuran (10 ml) at 25-30° C. Filtered the reaction mass through filter paper and washed with tetrahydrofuran (1 ml). Distilled off the solvent from the filtrate and unloaded the obtained compound to get the title compound. Yield: 0.8 g; water content: 0.8%.

The Powder X-ray diffraction pattern of the obtained compound is shown in FIG. 2.

Example-8: Preparation of amorphous 4-[4-({[4-chloro-3-(trifluoromethyl)phenyl]carbamoyl}amino)-3-fluorophenoxy]-N-methylpyridine-2-carboxamide premix Dissolved 4-[4-({[4-chloro-3-(trifluoromethyl)phenyl]carbamoyl}amino)-3-fluoro phenoxy]-N-methylpyridine-2-carboxamide (0.5 g) in methyl ethyl ketone (15 ml) at 25-30° C. Filtered the reaction mass through filter paper and washed with methyl ethyl ketone (1 ml). Microcrystalline cellulose (0.5 g) was added to the filtrate and stirred for 5 minutes at 25-30° C. Distilled off the solvent completely from the reaction mixture and unloaded the obtained compound to get title compound.

Yield: 0.8 g;

Example-9: Preparation of amorphous 4-[4-({[4-chloro-3-(trifluoromethyl)phenyl]carbamoyl}amino)-3-fluorophenoxy]-N-methylpyridine-2-carboxamide Dissolved 4-[4-({[4-chloro-3-(trifluoromethyl)phenyl]carbamoyl}amino)-3-fluorophenoxy]-N-methylpyridine-2-carboxamide (1 g) in a mixture of tetrahydrofuran (8 ml) and methanol (2 ml). The reaction mixture was stirred at 25-30° C. for 10-15 mins. Filtered the reaction mass through filter paper. Distilled off the solvent from the filtrate and unloaded the obtained compound to get the title compound.

Yield: 0.8 g; water content: 0.51%.

We claim:
1. A process for the preparation of 4-[4-({[4-chloro-3-(trifluoromethyl)phenyl]carbamoyl}amino)-3-fluorophenoxy]-N-methylpyridine-2-carboxamide compound of formula-1 substantially free of 4-(4-amino-3-fluorophenoxy)-N-methylpicolinamide compound of formula-4, comprising:
(a) reacting 4-chloro-N-methylpicolinamide compound of formula-2

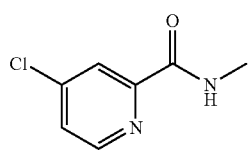

Formula-2 with 4-amino-3-fluorophenol compound of formula-3

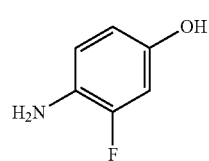

Formula-3 in presence of a suitable base in a suitable solvent in presence or absence of a suitable catalyst provides 4-(4-amino-3-fluorophenoxy)-N-methylpicolinamide compound of formula-4,

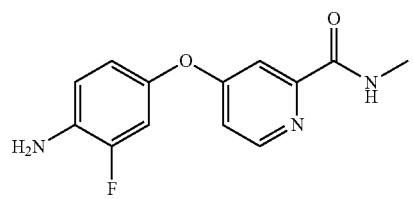

Formula-4

(b) adding first lot of compound of formula-4 to the first lot of 4-chloro-3-(trifloromethyl)phenyl isocyanate compound of formula-5

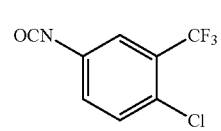

Formula-5 in dichloromethane,
(c) stirring the reaction mixture at a suitable temperature,
(d) adding second lot of 4-(4-amino-3-fluorophenoxy)-N-methylpicolinamide compound of formula-4 to the reaction mixture,
(e) stirring the reaction mixture at a suitable temperature and filtering the precipitated solid,
(f) dissolving the compound obtained in step-(e) in dimethylsulfoxide,
(g) adding second lot of 4-chloro-3-(trifloromethyl)phenyl isocyanate compound of formula-5 to the reaction mixture and stirring the reaction mixture at a suitable temperature,
(h) adding methanol to the reaction mixture,
(i) cooling and stirring the reaction mixture,
(j) filtering the precipitated solid and drying to get DMSO solvate of compound of formula-1,
(k) dissolving DMSO solvate obtained in step-(j) in dimethylsulfoxide,
(l) adding methanol to the reaction mixture and filtering the reaction mixture,
(m) stirring the reaction mixture at −15 to −25° C.,
(n) filtering the precipitated solid and drying the compound to get compound of formula-1,
(o) optionally, slurrying the solid obtained in step-(n) with methanol to provide compound of formula-1 substantially free of 4-(4-amino-3-fluorophenoxy)-N-methylpicolinamide compound of formula-4.

2. The process according to claim 1, wherein;
in step (a) the suitable temperature is 0-5° C.;
in step (e) the suitable temperature is 0-5° C.;
in step (g) the suitable temperature is 19-23° C.

3. The process according to step (j) of claim 1, wherein the DMSO solvate is in crystalline form, said crystalline form characterized by:
(a) a powder X-ray diffraction pattern having peaks at 7.3, 9.2, 11.0, 13.5, 14.6, 14.9, 16.5, 17.0, 17.3, 18.1, 19.0, 19.5, 19.9, 21.6, 23.8, 24.6, 24.9, 25.1, 26.1 and 27.5±0.2 degrees of 2-theta; and (b) a powder X-ray diffraction pattern as illustrated in FIG. 1.

4. The process according to claim 3, wherein the preparation of DMSO solvate comprises:
(a) adding first lot of 4-(4-amino-3-fluorophenoxy)-N-methylpicolinamide compound of formula-4 with 4-chloro-3-(trifloromethyl)phenyl isocyanate compound of formula-5 in a suitable solvent,
(b) stirring the reaction mixture at a suitable temperature,
(c) adding another lot of 4-(4-amino-3-fluorophenoxy)-N-methylpicolinamide compound of formula-4 to the reaction mixture,
(d) stirring the reaction mixture at a suitable temperature,
(e) filtering the solid obtained in step (d),
(f) dissolving the compound obtained in step (e) in dimethylsulfoxide,
(g) adding a suitable solvent to the reaction mixture,
(h) cooling and stirring the reaction mixture,
(i) filtering the solid and drying to get DMSO solvate of compound of formula-1.

5. The process according to claim 4, wherein;
in step-(b) the suitable temperature is 0-5° C.;
in step (d) the suitable temperature is 0-5° C.;
in step (g) the suitable solvent is methanol.

6. The process according to claim 4, wherein the process for the preparation of crystalline polymorph-I of 4-[4-({[4-chloro-3-(trifluoro methyl)phenyl]carbamoyl}amino)-3-fluorophenoxy]-N-methylpyridine-2-carboxamide compound of formula-1, comprising:
(a) dissolving the DMSO solvate in a suitable solvent,
(b) adding anti-solvent to the reaction mixture,
(c) cooling and stirring the reaction mixture at a suitable temperature,
(d) filtering the solid and drying the compound to get crystalline polymorph-I of compound of formula-1,
(e) optionally, slurrying the solid obtained in step-(d) with a suitable solvent to provide crystalline polymorph-I of compound of formula-1.

7. The process according to claim 6, wherein;
in step (a) the suitable solvent is dimethylsulfoxide;
in step (b) the suitable anti-solvent is methanol;
in step (c) the suitable temperature is −15 to −25° C.

8. The process according to claim 1, wherein the 4-[4-({[4-chloro-3-(trifluoromethyl)phenyl]carbamoyl} amino)-3-fluorophenoxy]-N-methylpyridine-2-carboxamide compound of formula-1 comprises a particle size distribution of $D(0.9) \leq 100$ μm and $D(4.3) \leq 50$ μm.

9. The process according to claim 1, wherein the 4-[4-({[4-chloro-3-(trifluoro methyl)phenyl]carbamoyl}amino)-3-fluorophenoxy]-N-methylpyridine-2-carboxamide compound of formula-1 comprises <10 ppm of 4-(4-amino-3-fluorophenoxy)-N-methyl picolinamide compound of formula-4 (amine impurity) and substantially free of 4-amino-3-fluorophenol impurity compound of formula-3, trifluoro impurity, methyl ester impurity and dimer impurity.

10. The process according to claim 1, wherein the 4-[4-({[4-chloro-3-(trifluoro methyl)phenyl]carbamoyl}amino)-3-fluorophenoxy]-N-methylpyridine-2-carboxamide compound of formula-1 comprises <10 ppm of chloro impurity compound of formula-2.

11. The process according to claim 1, wherein the 4-[4-({[4-chloro-3-(trifluoromethyl)phenyl] carbamoyl}amino)-3-fluorophenoxy]-N-methylpyridine-2-carboxamide compound of formula-1 comprises ≤20 ppm of 4-(4-amino-3-fluorophenoxy)-N-methylpicolinamide compound of formula-4.

\* \* \* \* \*